(12) United States Patent
Lo

(10) Patent No.: US 6,193,687 B1
(45) Date of Patent: Feb. 27, 2001

(54) SAFETY HYPODERMIC SYRINGE

(75) Inventor: Cheng-Chi Lo, Yungho (TW)

(73) Assignee: Pi-Chang Lo, Taipei (TW)

( * ) Notice: Subject to any disclaimer, the term of this patent is extended or adjusted under 35 U.S.C. 154(b) by 0 days.

(21) Appl. No.: 09/621,822

(22) Filed: Jul. 21, 2000

(30) Foreign Application Priority Data

Jan. 25, 2000 (TW) .................................. 89201289
May 22, 2000 (TW) .................................. 89208653

(51) Int. Cl.[7] ........................................ A61M 5/00

(52) U.S. Cl. .................................. 604/110; 604/195

(58) Field of Search .................... 604/110, 187, 604/195, 240, 241, 242

(56) References Cited

U.S. PATENT DOCUMENTS

| 5,634,903 | * | 6/1997 | Kurose et al. | ........................ 604/110 |
| 5,645,535 | * | 7/1997 | Goldberg | ............................... 604/195 |
| 5,693,023 | * | 12/1997 | Adams | ................................. 604/195 |
| 5,820,605 | * | 10/1998 | Zdeb | ................................. 604/110 X |

* cited by examiner

Primary Examiner—John D. Yasko
(74) Attorney, Agent, or Firm—Bacon & Thomas, PLLC

(57) ABSTRACT

A safety hypodermic syringe is constructed to include a barrel, a needle assembly, a female connector, a plunger, and a male connector, wherein the female connector is disposed in the front end of the barrel and fastened to the needle assembly, having a rear retaining hole; the male connector is provided at the front side of the plunger and adapted to engage the rear retaining hole upon forward stroke of the plunger, for enabling the needle assembly to be pulled backwards with the plunger and received inside the barrel after the service of the hypodermis syringe.

6 Claims, 8 Drawing Sheets

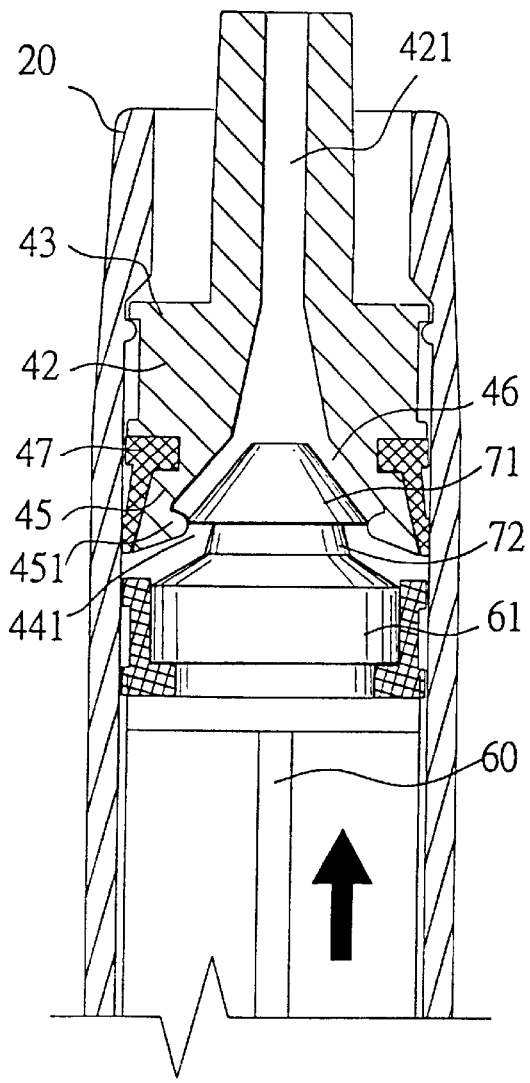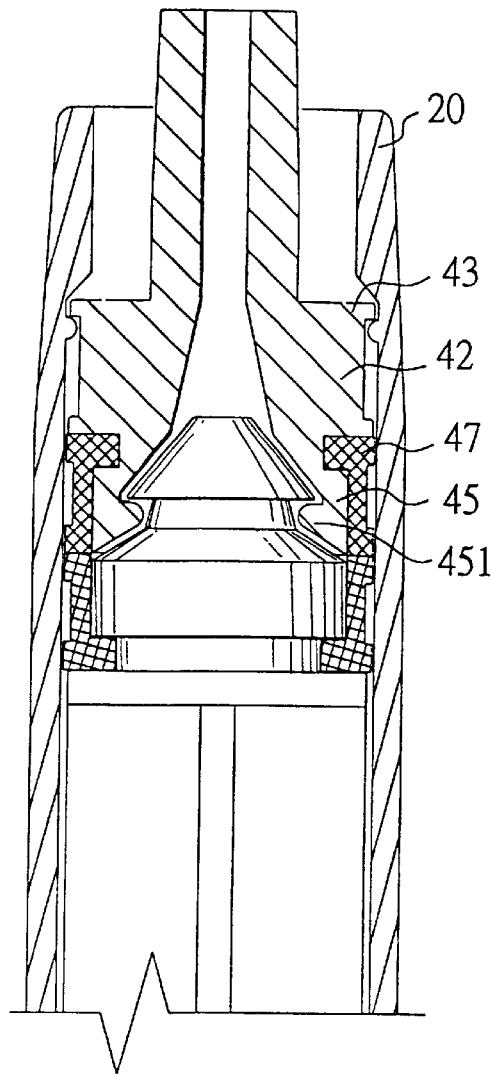
Fig. 11                    Fig. 12

SAFETY HYPODERMIC SYRINGE

BACKGROUND OF THE INVENTION

The present invention relates to a hypodermic syringe, and more particularly to a safety hypodermic syringe, which enables the needle assembly to be received inside the syringe barrel after the service of the syringe.

Regular safety hypodermic syringes are made for enabling the user (nurse or doctor) to pull the needle assembly backwards to the inside of the syringe barrel after injection, preventing possible contamination of bacteria or virus through the needle cannula. Taiwan Patent #356013 discloses a similar design of safety hypodermic syringe. However, this design of safety hypodermic syringe is still not satisfactory in function. When pushing the plunger into engagement with the needle assembly, a minor vibration occurs, causing the patient to feel uncomfortable.

SUMMARY OF THE INVENTION

The invention has been accomplished under the circumstances in view. It is one object of the present invention to provide a safety hypodermic syringe, which enables the needle assembly to be pulled backwards and received inside the syringe barrel after the use of the syringe. It is another object of the present invention to provide a safety hypodermic syringe, which eliminates the occurrence of vibration during injection. It is still another object of the present invention to provide a safety hypodermic syringe, which saves much fabrication time, and reduces the manufacturing cost. According to the present invention, the safety hypodermic syringe comprises a barrel, a needle assembly, a female connector, a plunger, and a male connector. The needle assembly is disposed at the front side of the barrel, and connected to the front side of the female connector. The female connector has a rear retaining hole that can be radially reduced or expanded, and a rear side mounted with an elastic band. The elastic band imparts a radial compression force to the rear part of the female connector, causing the rear retaining hole to be reduced to the smallest status. The elastic band can be molded from rubber or other equivalent material. The male connector comprises a shank forwardly extended from the front side of the plunger, and a head at the front end of the shank. When pushing the plunger forwards in the barrel, the head of the male connector is forced to expand the rear retaining hole. After passed through the rear retaining hole, the rear retaining hole is reduced to stop the head of the male connector from backward movement, and therefore the needle assembly and the female connector are moved backwards with the male connector and received inside the barrel when pulling the plunger backwards to the rear end of the barrel. Because the opening status of the retaining hole is controlled by the elastic band, little vibration is produced when engaging the head of the male connector into the retaining hole of the female connector.

BRIEF DESCRIPTION OF THE DRAWINGS

FIG. 11 is a sectional view of a part of the safety hypodermic syringe according to the second embodiment of the present invention, showing the head of the male connector inserted into the retaining hole of the female connector.

FIG. 12 is similar to FIG. 11 but showing the head of the male connector passed over the hooks of the stop blocks and engaged with the retaining hole of the female connector.

DETAILED DESCRIPTION OF THE PREFERRED EMBODIMENT

Figure 1:
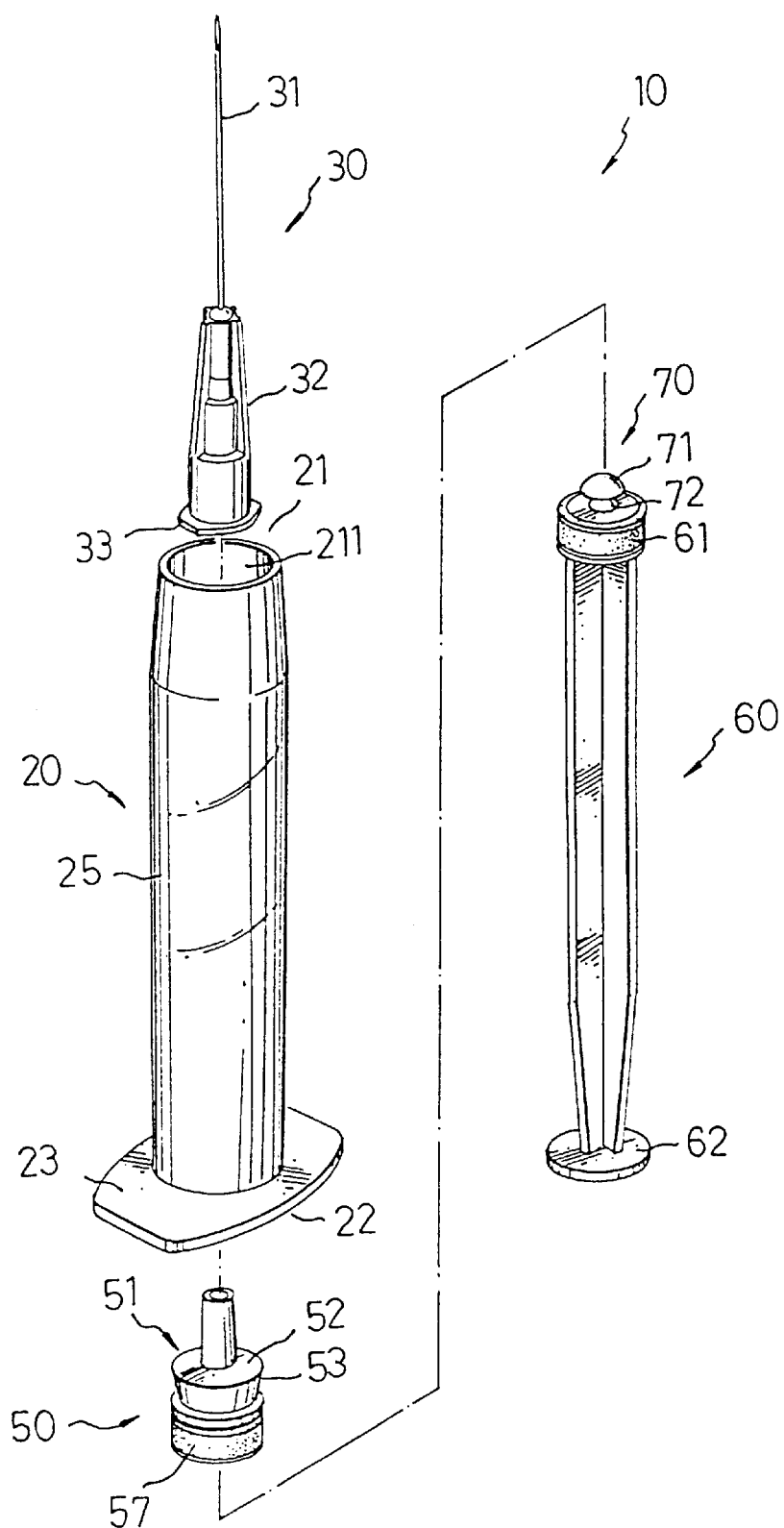
FIG. 1 is an exploded view of a safety hypodermic syringe according the present invention.

Referring to FIGS. from 1 through 8, a safety hypodermic syringe 10 is shown comprised of a barrel 20, a needle assembly 30, a female connector 50, a plunger 60, and a male connector 70.

The barrel 20 comprises a cylindrical body 25, and a finger flange 23 integral with the rear end 22 of the body 25. The body 25 has a front opening 211 at the tapered front end 21 thereof, a rear opening 221 at the rear end 22 thereof, an inside receiving chamber 24 in communication between the front opening 211 and the rear opening 221, and an annular inside stop flange 26 raised around the inside wall thereof within the inside receiving chamber 24 adjacent to the front opening 211, and another annular inside step flange 27 raised around the inside wall of the rear end thereof within the inside receiving chamber 24 adjacent to the finger flange 23.

The needle assembly 30 comprises a needle cannula 31 and a needle hub 32 holding the needle cannula 31. The needle hub 32 has a locating flange 33 raised around the periphery of the rear end thereof. The diameter of the locating flange 33 is greater than the inner diameter of the annular inside stop flange 26, so that the locating flange 33 can be positively stopped behind the annular inside stop flange 26 after installation of the needle assembly 30 in the front end 21 of the barrel 20. The connection between the needle cannula 31 and the needle hub 32 can easily be achieved by conventional techniques. Further, any equivalent structural design can be employed instead of the matching of the annular inside stop flange 26 and the locating flange 33.

Figure 3:
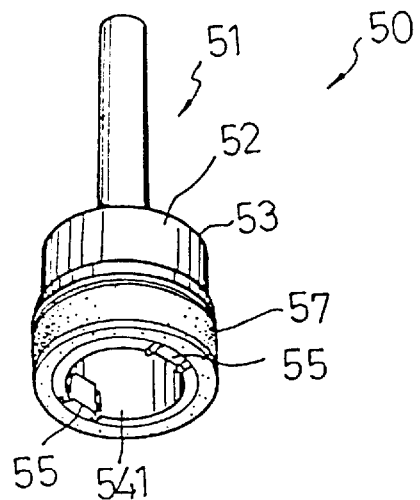
FIG. 3 is a perspective assembly view of the female connector shown in FIG. 2.
Figure 2:
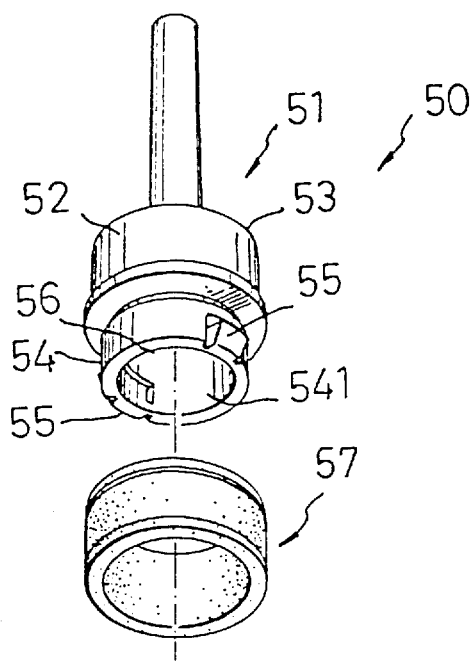
FIG. 2 is an exploded view of a female connector according to a first embodiment of the present invention.

The female connector 50 fits the inside wall of the barrel 20 around the receiving chamber 24. According to the present preferred embodiment, the female connector 50 comprises a hollow connector body 51 defining a chamber 56, and an elastic band 57 mounted on the connector body 51 (see FIGS. 2 and 3). The connector body 51 comprises a front needle hub support part 52 having a front hole 521, and a rear male connector receiving part 54 having a retaining hole 541. The front needle hub support part 52 is coupled to the rear side of the needle hub 32 of the needle assembly 30. According to the present preferred embodiment, the front needle hub support part 52 is a hollow, stepped member fitted into the needle hub 32 from the rear side of the needle hub 32, having a step 53 stopped at the locating flange 33 against the annular inside stop flange 26 to seal the gap and to prevent the fluid (medicine or blood) from leaking out of the hypodermic syringe. Alternatively, an O-ring may be used to seal the gap. The rear male connector receiving part 54 is disposed at the rear side of the front needle hub support part 52. According to the present preferred embodiment, the rear male connector receiving part 54 and the rear side of the front needle hub support part 52 are made in integrity. The rear male connector receiving part 54 comprises two equi-angularly spaced (spaced from each other at 180°) springy stop blocks 55. The stop blocks 55 each have a part connected to the rear connector receiving part 54. The elastic band 57 is mounted on the rear male connector receiving part 54 over the stop blocks 55 (see FIG. 3). After installation of the elastic band 57, stop blocks 55 are forced inwards into the chamber 56. The elastic band 57 is preferably molded from rubber. The number of the stop blocks 55 may be changed as desired. For example, three, four, five or more stop blocks 55 may be provided. However, the stop blocks 55 must be equiangularly spaced from one another. In case three stop blocks 55 are provided, the stop blocks 55 must be equally spaced at the internal of 120°.

The plunger 60 is inserted from the rear opening 221 into the body 25 of the barrel 20, having a front end fixedly mounted with a stopper 61 and a rear end terminating in a thumb rest 62.

The male connector 70 is installed in the front side of the plunger 60 and protruded over the front side of the stopper 61. According to the present preferred embodiment, the male connector 70 is shaped like a parachute (mushroom), comprising a head 71 and a shank 72. The head 71 is fixedly connected to one end, namely, the front end of the shank 72, having a smaller front part and a greater rear part. The cross-sectional area of the rear part of the head 71 is greater than the retaining hole 541 defined after the stop blocks 55 has been forced into the chamber 56.

Figure 4:
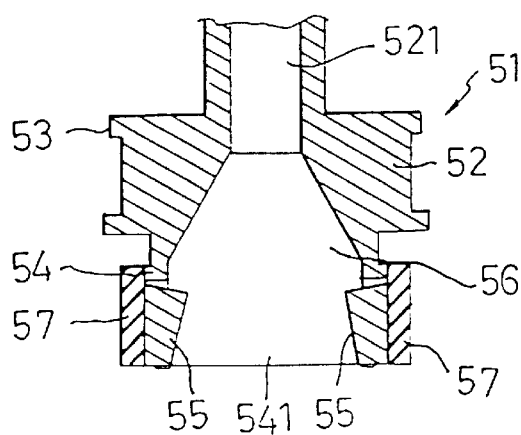
FIG. 4 is a sectional view showing the status of the female connector before the insertion of the male connector.

During injection and before moving the male connector 70 into engagement with the female connector 50 (the male connector 70 can be made having a split for easy insertion into the female connector 50 with less insertion resistance), as shown in FIG. 4, the stop blocks 55 are forced by the compressive force of the elastic band 57 to project into the chamber 56, defining the aforesaid retaining hole 541.

Figure 5:
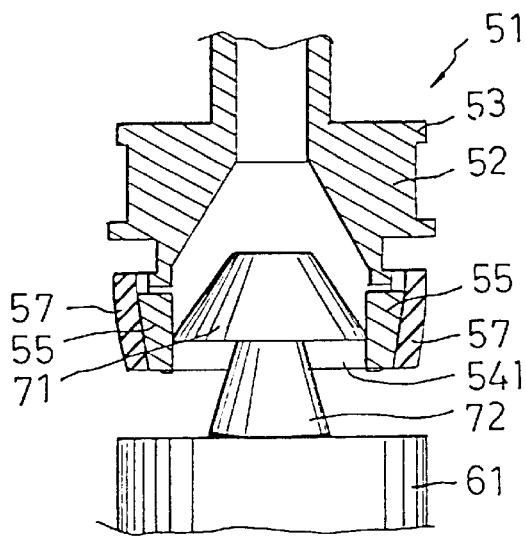
FIG. 5 is a sectional view showing the head of the male connector inserted into the retaining hole of the female connector according to the present invention.

When forcing the male connector 70 into the retaining hole 541, as shown in FIG. 5, the stop blocks 55 are forced radially outwards by the greater rear part of the head 71 of the male connector 70 to expand the elastic band 57. When the elastic band 57 expands, it buffers (smoothens) the radially outwardly displacement of the stop blocks 55, preventing the occurrence of vibration.

Figure 6:
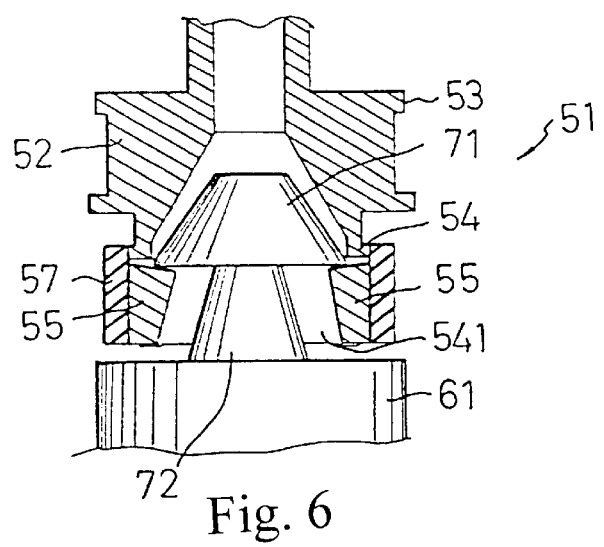
FIG. 6 is a sectional view showing the head of the male connector passed through the retaining hole into the chamber inside the female connector according to the present invention.
Figure 7:
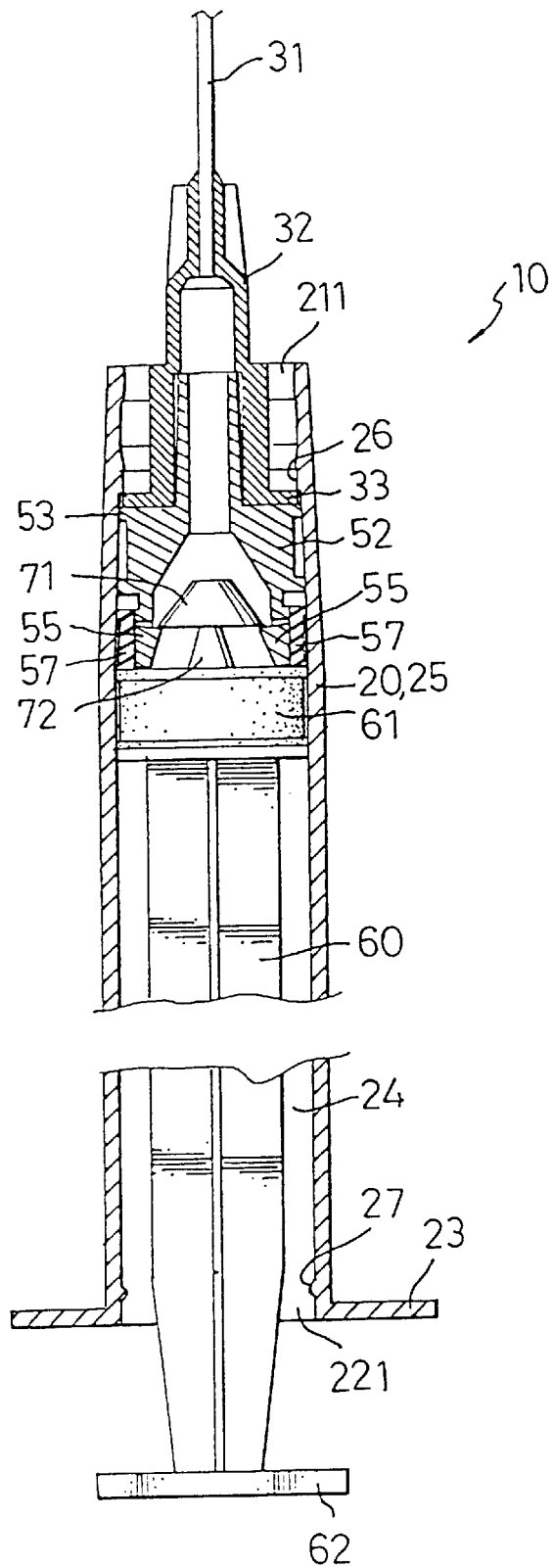
FIG. 7 is a sectional view of the safety hypodermic syringe according to the first embodiment of the present invention, showing the plunger pushed to the front limit position in the barrel.

After the head 71 of the male connector 70 passed the retaining hole 541, as shown in FIG. 6, the elastic band 57 is released from pressure and returns to its former shape to force the stop blocks 55 back to their former positions smoothly, as shown in FIG. 7, eliminating possible shocks.

Figure 8:
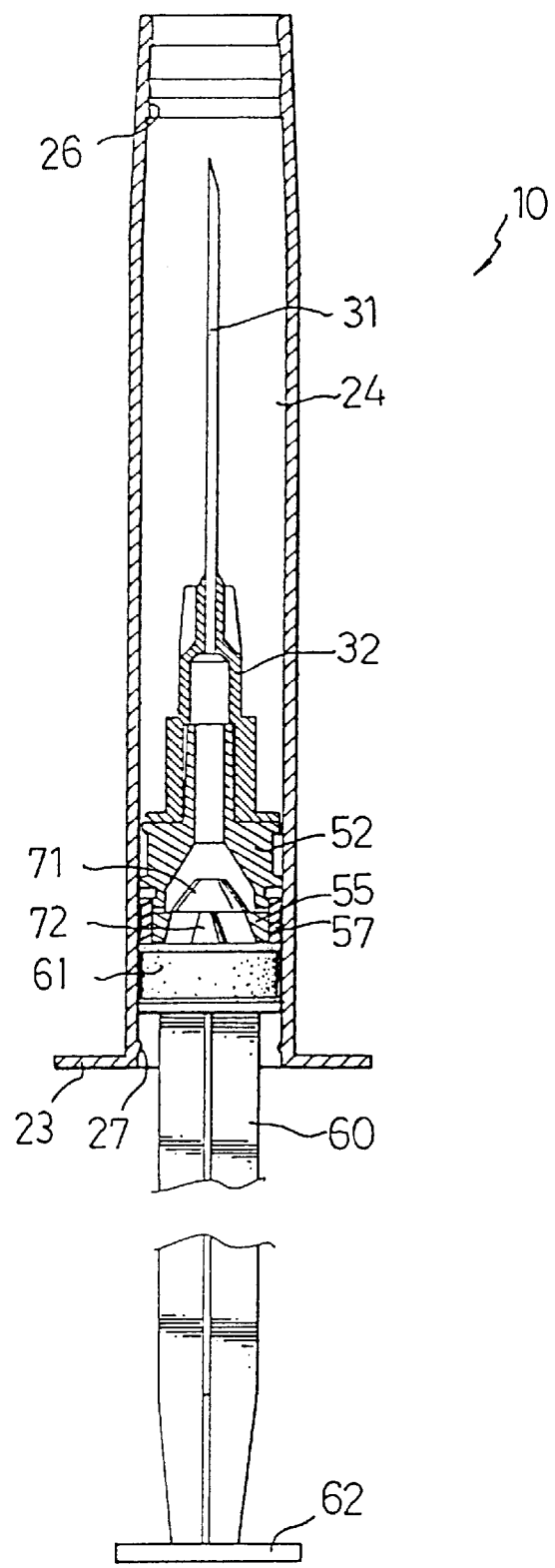
FIG. 8 is another sectional view of the safety hypodermic syringe according to the first embodiment of the present invention, showing the plunger moved to the rear limit position in the barrel and the needle assembly received inside the barrel.
Figure 9:
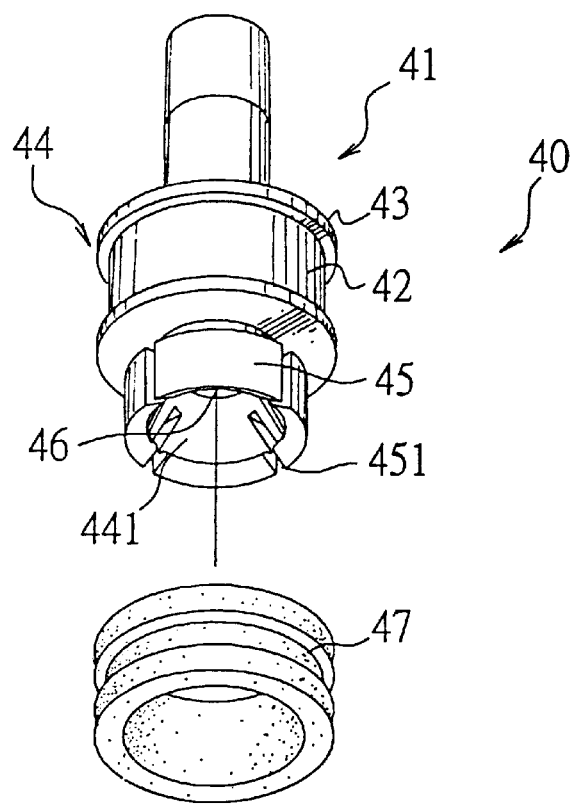
FIG. 9 is an exploded view of a female connector for a safety hypodermic syringe according to a second embodiment of the present invention.
Figure 10:
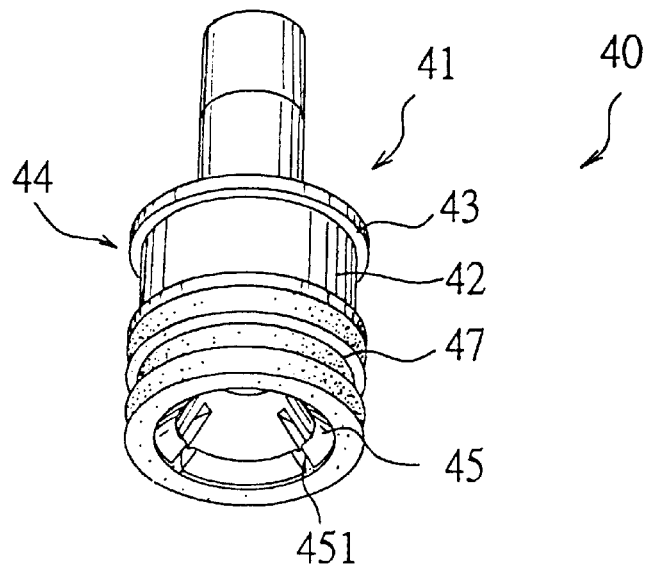
FIG. 10 is a perspective assembly view of the female connector shown in FIG. 9.

When the user pulls the plunger 60 backwards after injection, the female connector 50 and the needle assembly 30 are moved backwards with the male connector 70 and plunger 60 and received in the inside receiving chamber 24 inside the barrel 20 as shown in FIG. 8, and therefore the needle cannula 31 is well protected inside the barrel 20.

FIGS. from 9 through 13 show a second embodiment of the present invention. The second embodiment has similar structure as the aforesaid first embodiment with the exception of the female connector. According to the second embodiment, the female connector, referenced by 40 comprises a hollow connector body 41 defining a chamber 46, and an elastic band 47 mounted on the connector body 41. The connector body 41 comprises a front needle hub support part 42 having a front hole 421, and a rear male connector receiving part 44 having a retaining hole 441. The front needle hub support part 42 is coupled to the rear side of the needle hub 32 of the needle assembly 30. The front needle hub support part 42 is a hollow, stepped member fitted into the needle hub 32 from the rear side of the needle hub 32, having a step 43 stopped at the locating flange 33 against the annular inside stop flange 26 to seal the gap. The rear male connector receiving part 44 comprises four equiangularly spaced springy stop blocks 45. The stop blocks 45 each have an inward hook 451 facing the chamber 46. Before engaging the head 71 of the male connector 70, the cross-sectional area of the retaining hole 441 defined within the hooks 451 of the stop blocks 45 is smaller than the greatest cross-sectional area of the head 71 of the male connector 70.

Figure 13:
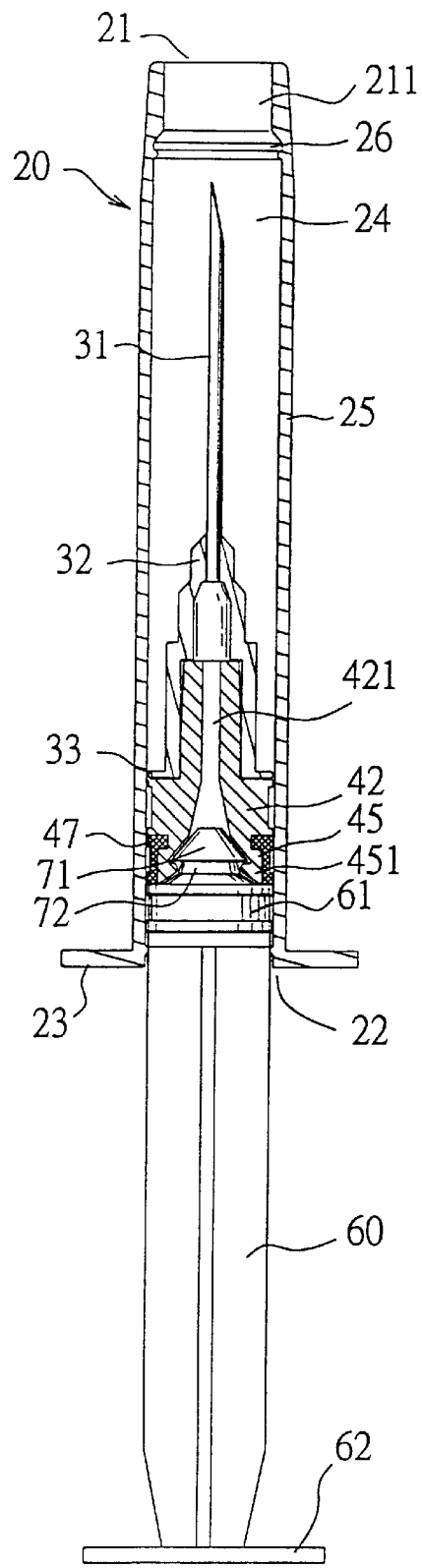
FIG. 13 is a sectional view of the second embodiment of the present invention, showing the plunger moved to the rear limit position in the barrel and the needle assembly received inside the barrel.

As illustrated in FIG. 11, when the head 71 is moved with the plunger 60 forwards to squeeze the hooks 451 of the stop blocks 45, the stop blocks 45 are forced radially outwards to expand the elastic band 47 for enabling the head 71 of the male connector 70 to pass through the retaining hole 441 into the chamber 46, as shown in FIG. 12. When the user pulls the plunger 60 backwards after the service of the hypodermic syringe, the female connector 40 and the needle assembly 30 are moved backwards with the male connector 70 and plunger 60 and received in the inside receiving chamber 24 inside the barrel 20 as shown in FIG. 13, and therefore the needle cannula 31 is well protected inside the barrel 20.

According to the second embodiment of the present invention, the elastic band 47 is preferably molded from natural rubber and then mounted on the rear male connector receiving part 44. In order to save manufacturing cost and time, the elastic band 47 can be directly injection-molded on the outside of the rear male connector receiving part 44 after molding of the connector body 41.

It is to be understood that the drawings are designed for purposes of illustration only, and are not intended for use as a definition of the limits and scope of the invention disclosed.

What the invention claimed is:

1. A safety hypodermic syringe comprising:
   a barrel defining a cylindrical inside receiving chamber;
   a needle assembly, said needle assembly comprising a hollow needle hub, and a needle cannula, said needle cannula having one end fastened to said needle hub;
   a female connector slidably fitting the cylindrical inside receiving chamber of said barrel, said female connector comprising a connector body and an elastic band, said connector body comprising a front needle hub support part fastened to said needle hub of said needle assembly, a rear male connector receiving part connected to said front needle hub support part, a front hole at a front side of said front needle hub support part, a rear retaining hole at a rear side of said rear male connector receiving part, and a chamber in communication between said front hole and said rear retaining hole, said rear male connector receiving part comprising a plurality of springy stop blocks radially moved to reduce/expand said rear retaining hole radially, said elastic band being mounted on said rear male connector receiving part;

a plunger, said plunger comprising a stopper at a front side thereof, and a thumb rest at a rear side thereof; and a male connector installed in the front side of said plunger and protruded over a front side of said stopper, said male connector comprising a shank forwardly extended from said stopper, and a head fixedly connected to a front end of said shank, said head having a small front part and a big rear part greater than said small front part, said retaining hole having a cross-sectional area smaller than the cross-sectional area of the big rear part of said head when radially reduced by said stop blocks.

2. The safety hypodermic syringe of claim 1 wherein said stop blocks protrude from an inside wall of said rear male connector receiving part into the chamber.

3. The safety hypodermic syringe of claim 1 wherein said stop blocks each comprise an inward hook projecting toward the chamber.

4. The safety hypodermic syringe of claim 1 wherein said stop blocks are equiangularly arranged around the periphery of said rear male connector receiving part.

5. The safety hypodermic syringe of claim 1 wherein said elastic band is sleeved onto said rear male connector receiving part.

6. The safety hypodermic syringe of claim 1 wherein said elastic band is injection-molded on said stop blocks outside said rear male connector receiving part.

* * * * *